US012599304B2

(12) United States Patent (10) Patent No.: US 12,599,304 B2
Felix et al. (45) Date of Patent: *Apr. 14, 2026

(54) CONFIGURABLE HARDWARE PLATFORM FOR PHYSIOLOGICAL MONITORING OF A LIVING BODY

(71) Applicant: Bardy Diagnostics, Inc., Bellevue, WA (US)

(72) Inventors: Jason Felix, Vashon Island, WA (US); Joshua Djon Green, Seattle, WA (US); Corey B. Williamson, Bellingham, WA (US); Gust H. Bardy, Carnation, WA (US)

(73) Assignee: Bardy Diagnostics, Inc., Bellevue, WA (US)

( * ) Notice: Subject to any disclaimer, the term of this patent is extended or adjusted under 35 U.S.C. 154(b) by 199 days.

This patent is subject to a terminal disclaimer.

(21) Appl. No.: 18/349,544

(22) Filed: Jul. 10, 2023

(65) Prior Publication Data

US 2023/0363641 A1 Nov. 16, 2023

Related U.S. Application Data

(63) Continuation of application No. 16/929,390, filed on Jul. 15, 2020, now Pat. No. 11,696,681, which is a
(Continued)

(51) Int. Cl.
*A61B 5/00* (2006.01)
*A61B 5/0205* (2006.01)
(Continued)

(52) U.S. Cl.
CPC .......... *A61B 5/0006* (2013.01); *A61B 5/0022* (2013.01); *A61B 5/0031* (2013.01);
(Continued)

(58) Field of Classification Search
CPC .......... A61B 2560/0219; A61B 5/0031; A61B 5/02055; A61B 5/0205; A61B 5/073; A61B 5/076; A61B 5/07
See application file for complete search history.

(56) References Cited

U.S. PATENT DOCUMENTS 5,862,803 A 1/1999 Besson et al.
7,197,357 B2 3/2007 Istvan et al.
(Continued)

FOREIGN PATENT DOCUMENTS

WO WO 03/065926 A2 8/2003
WO WO 2008/005015 A1 1/2008
WO WO 2010/104952 A2 9/2010

OTHER PUBLICATIONS

Anand et al., "Design of the Multi-Sensor Monitoring in Congestive Heart Failure (MUSIC) Study: Prospective Trial to Assess the Utility of Continuous Wireless Physiologic Monitoring in Heart Failure", Journal of Cardiac Failure, vol. 17, No. 1, Jan. 1, 2011, pp. 11-16 (6 pages).
(Continued)

*Primary Examiner* — Tse W Chen
*Assistant Examiner* — Michael A Catina
(74) *Attorney, Agent, or Firm* — K&L Gates LLP

(57) ABSTRACT

An implantable medical device is disclosed. A housing includes a hollow body forming a first electrode on an outer surface with end caps affixed to opposite ends, one end cap forming a second electrode. A microcontroller circuit is provided and includes a microcontroller operable under program instructions stored within a non-volatile memory device. An analog front end is interfaced to the electrodes to sense electrocardiographic signals. A transceiver circuit is operable to wirelessly communicate with an external data device. The program instructions define instructions to continuously sample the electrocardiographic signals into the
(Continued)

<u>10</u> non-volatile memory device and to offload the non-volatile memory device to the external data device. A receiving coil and a charging circuit are operable to charge an onboard power source for the microcontroller circuit.

19 Claims, 8 Drawing Sheets

Related U.S. Application Data continuation-in-part of application No. 16/926,381, filed on Jul. 10, 2020, now Pat. No. 11,096,579, which is a continuation-in-part of application No. 16/919,626, filed on Jul. 2, 2020, now Pat. No. 11,116,451.

(60) Provisional application No. 62/962,773, filed on Jan. 17, 2020, provisional application No. 62/874,086, filed on Jul. 15, 2019, provisional application No. 62/873,740, filed on Jul. 12, 2019, provisional application No. 62/873,754, filed on Jul. 12, 2019, provisional application No. 62/870,506, filed on Jul. 3, 2019.

(51) Int. Cl.
| | |
|---|---|
| *A61B 5/07* | (2006.01) |
| *A61B 5/287* | (2021.01) |
| *G16H 40/67* | (2018.01) |
| *G16H 50/20* | (2018.01) |
| *G16H 80/00* | (2018.01) |
| *H04L 12/28* | (2006.01) |
| *H04Q 9/02* | (2006.01) |
| *A61B 5/021* | (2006.01) |
| *A61B 5/08* | (2006.01) |
| *A61B 5/087* | (2006.01) |
| *A61B 5/145* | (2006.01) |
| *A61B 5/1455* | (2006.01) |

(52) U.S. Cl.
CPC .......... *A61B 5/02055* (2013.01); *A61B 5/073* (2013.01); *A61B 5/287* (2021.01); *G16H 40/67* (2018.01); *G16H 50/20* (2018.01); *G16H 80/00* (2018.01); *H04L 12/2825* (2013.01); *H04Q 9/02* (2013.01); *A61B 5/021* (2013.01); *A61B 5/0816* (2013.01); *A61B 5/087* (2013.01); *A61B 5/14532* (2013.01); *A61B 5/14552* (2013.01); *A61B 2560/0219* (2013.01); *A61B 2562/0219* (2013.01); *H04Q 2209/886* (2013.01)

(56) References Cited

U.S. PATENT DOCUMENTS

| | | | |
|---|---|---|---|
| 7,206,630 | B1 | 4/2007 | Tarler |
| 7,212,849 | B2 | 5/2007 | Zhang et al. |
| 7,294,108 | B1 | 11/2007 | Bornzin et al. |
| 7,395,106 | B2 | 7/2008 | Ryu et al. |
| 7,468,032 | B2 | 12/2008 | Stahmann et al. |
| 8,150,502 | B2 | 4/2012 | Kumar et al. |
| 8,214,007 | B2 | 7/2012 | Baker et al. |
| 8,315,695 | B2 | 11/2012 | Sebelius et al. |
| 8,483,809 | B2 | 7/2013 | Kim et al. |
| 8,538,503 | B2 | 9/2013 | Kumar et al. |
| 8,611,980 | B2 | 12/2013 | Choe et al. |
| 8,647,268 | B2 | 2/2014 | Tran |
| 8,718,742 | B2 | 5/2014 | Beck et al. |
| 8,926,509 | B2 | 1/2015 | Magar et al. |
| 9,211,073 | B2 | 12/2015 | Banet et al. |
| 9,277,864 | B2 | 3/2016 | Yang et al. |
| 9,510,755 | B2 | 12/2016 | Fong et al. |
| 9,669,212 | B2 | 6/2017 | Mueller et al. |
| 10,327,660 | B2 | 6/2019 | Gallego et al. |
| 10,413,251 | B2 | 9/2019 | Golda et al. |
| 10,441,185 | B2 | 10/2019 | Rogers et al. |
| 11,051,743 | B2 | 7/2021 | Felix et al. |
| 11,116,447 | B2 | 9/2021 | Yang et al. |
| 11,445,967 | B2 | 9/2022 | Felix et al. |
| 2008/0091089 | A1 | 4/2008 | Guillory et al. |
| 2009/0062670 | A1 | 3/2009 | Sterling et al. |
| 2009/0099469 | A1 | 4/2009 | Flores |
| 2009/0177073 | A1 | 7/2009 | Sonnenborg |
| 2009/0182204 | A1 | 7/2009 | Semler et al. |
| 2011/0009729 | A1 | 1/2011 | Shin et al. |
| 2011/0054285 | A1 | 3/2011 | Searle et al. |
| 2011/0077497 | A1 | 3/2011 | Oster et al. |
| 2011/0125040 | A1 | 5/2011 | Crawford et al. |
| 2012/0323098 | A1 | 12/2012 | Moein et al. |
| 2013/0225967 | A1 | 8/2013 | Esposito |
| 2015/0022372 | A1 | 1/2015 | Vosch |
| 2015/0087950 | A1 | 3/2015 | Felix et al. |
| 2017/0065207 | A1* | 3/2017 | Landherr ............. A61B 5/0031 |
| 2018/0042552 | A1 | 2/2018 | Li et al. |
| 2018/0078771 | A1* | 3/2018 | Koop ................... A61B 5/6886 |
| 2018/0264258 | A1 | 9/2018 | Cheng et al. |
| 2019/0069815 | A1 | 3/2019 | Burnes et al. |
| 2019/0223806 | A1 | 7/2019 | Bennet et al. |

OTHER PUBLICATIONS

Cesario et al., "Arrhythmia Detection with a Low-Profile Wireless Adherent Cardiac Monitor: Results from the ADAM and EVE Studies", The Journal of Innovations in Cardiac Rhythm Management, Feb. 2011 Sep. 2011, pp. 476-482, (7 pages).

Corventis Nuvant, "Nuvant Mobile Cardiac Telemetry (MTC) System", Corventis, 2009, last printed Jul. 18, 2024, https://web.archive.org/web/20100127193736/http://corventis.com/AP/nuvant.asp.

Corventis Avivo, "Avivo Mobile Patient Management System", Corventis, 2008, lasted printed Jul. 18, 2024, https://web.archive.org/web/20100118155329/http://www.corventis.com/AP/avivo.asp.

IRhythm Zio XT Patch/Event Card, "Zio Patch", iRhythm, 2011, last printed Jul. 18, 2024, https://web.archive.org/web/20111017074139/http://irhythmtech.com/media/files/Z100A4020.04%20-%20ZIO%20PATCH%20DATA%20SHEET.pdf.

*Bardy Diagnostics, Inc.* v. *Vital Connect, Inc.*, Defendant's Identification of Supplemental Prior Art References, C.A. No. 22-351 (CJV), May 22, 2024.

International Preliminary Report on Patentability and Written Opinion, PCT/US2019/064331, Jun. 8, 2021.

First Examination Report, Communication pursuant to Article 94(3) EPC, 19 828 053.9-1113, dated Apr. 15, 2024.

[Corrected] Chart CC-2 Invalidity Contentions: U.S. Pat. No. 11,445,967; Case No. 22-351-CJB (Delaware); Invalidity of U.S. Patent No. by U.S. Pat. Pub. No. 2011/0077497 ("Oster") and U.S. Pat. No. 11,116,447 ("Yang"); Oct. 25, 2023; 16 pages.

[Corrected] Chart C-2 Invalidity Contentions: U.S. Pat. No. 11,051,743; Case No. 22-351-CJB (Delaware); Invalidity of U.S. Pat. No. 11,051,743 by U.S. Pat. Pub. No. 2011/0077497 ("Oster") and U.S. Pat. No. 11,116,447 ("Yang"); Oct. 25, 2023; 22 pages.

Chart AA-1 Invalidity Contentions: U.S. Pat. No. 11,445,967; Case No. 22-351-CJB (Delaware); Invalidity of U.S. Pat. No. 11,445,967 by International Publication No. WO 2010/104952 to Mazar ("Mazar") and U.S. Pat. No. 11,116,447 ("Yang"); Oct. 25, 2023; 24 pages.

Chart C-1 Invalidity Contentions: U.S. Pat. No. 11,051,743; Case No. 22-351-CJB (Delaware); Invalidity of U.S. Pat. No. 11,051,743 by International Publication No. WO 2010/104952 to Mazar ("Mazar") and U.S. Pat. No. 11,116,447 ("Yang"); Oct. 25, 2023; 32 pages.

Chart B-7 Invalidity Contentions: U.S. Pat. No. 11,051,743 and U.S. Pat. No. 11,445,967; Case No. 22-351-CJB (Delaware); A Patch Comprising Adhered Layers; Oct. 25, 2023; 16 pages.

Chart B-6 Invalidity Contentions: U.S. Pat. No. 11,051,743 and U.S. Pat. No. 11,445,967; Case No. 22-351-CJB (Delaware); Hydrocolloid Adhesives on a Portion of the Backing; Oct. 25, 2023; 5 pages.

(56) References Cited

OTHER PUBLICATIONS

Chart B-5 Invalidity Contentions: U.S. Pat. No. 11,051,743 and U.S. Pat. No. 11,445,967; Case No. 22-351-CJB (Delaware); Conversion of Electrocardiographic Signals From One Format to Another; Oct. 25, 2023; 6 pages.

Chart B-4 Invalidity Contentions: U.S. Pat. No. 11,051,743 and U.S. Pat. No. 11,445,967; The Case No. 22-351-CJB (Delaware); Rounded Outer Edge of Backing Ends; Oct. 25, 2023; 5 pages.

Chart B-3 Invalidity Contentions: U.S. Pat. No. 11,051,743 and U.S. Pat. No. 11,445,967; Case No. 22-351-CJB (Delaware); Flexible Circuit Comprising a Pair of Circuit Traces To Couple Electrodes; Oct. 25, 2023; 8 pages.

Chart B-2 Invalidity Contentions: U.S. Pat. No. 11,051,743 and U.S. Pat. No. 11,445,967; Case No. 22-351-CJB (Delaware); An Electrocardiographic Electrode On Each End Of The Backing; Oct. 25, 2023; 8 pages.

Chart B-1 Invalidity Contentions: U.S. Pat. No. 11,051,743 and U.S. Pat. No. 11,445,967; Case No. 22-351-CJB (Delaware); Elongated Strip With Narrowed Midsection; Oct. 25, 2023; 8 pages.

Chart AA-10 Invalidity Contentions: U.S. Pat. No. 11,445,967; Case No. 22-351-CJB (Delaware); Invalidity of U.S. Pat. No. 11,445,967 by WO 2003/065926 ("Ozguz"); Oct. 25, 2023; 6 pages.

Chart AA-9 Invalidity Contentions: U.S. Pat. No. 11,445,967; Case No. 22-351-CJB (Delaware); Invalidity of U.S. Pat. No. 11,445,967 by U.S. Pat. Pub. No. 2011/0009729 ("Shin"); Oct. 25, 2023; 6 pages.

Chart AA-8 Invalidity Contentions: U.S. Pat. No. 11,445,967; Case No. 22-351-CJB (Delaware); Invalidity of U.S. Pat. No. 11,445,967 by WO 2008/005015 ("Shennib"); Oct. 25, 2023; 6 pages.

Chart AA-7 Invalidity Contentions: U.S. Pat. No. 11,445,967; Case No. 22-351-CJB (Delaware); Invalidity of U.S. Pat. No. 11,445,967 by U.S. Pat. No. 7,206,630 ("Tarler"); Oct. 25, 2023; 7 pages.

Chart AA-6 Invalidity Contentions: U.S. Pat. No. 11,445,967; Case No. 22-351-CJB (Delaware); Invalidity of U.S. Pat. No. 11,445,967 by U.S. Pat. No. 9,669,212 ("Mueller"); Oct. 25, 2023; 6 pages.

Chart AA-5 Invalidity Contentions: U.S. Pat. No. 11,445,967; Case No. 22-351-CJB (Delaware); Invalidity of U.S. Pat. No. 11,445,967 by U.S. Pat. No. 10,413,251 ("Golda"); Oct. 25, 2023; 6 pages.

Chart A-4 Invalidity Contentions: U.S. Pat. No. 11,445,967; Case No. 22-351-CJB (Delaware); Invalidity of U.S. Pat. No. 11,445,967 by U.S. Pat. Pub. No. 2011/0077497 ("Oster"); Oct. 25, 2023; 6 pages.

Chart A-3 Invalidity Contentions: U.S. Pat. No. 11,445,967; Case No. 22-351-CJB (Delaware); Invalidity of U.S. Pat. No. 11,445,967 by U.S. Pat. No. 10,327,660 ("Gallego"); Oct. 25, 2023; 7 pages.

Chart AA-2 Invalidity Contentions: U.S. Pat. No. 11,445,967; Case No. 22-351-CJB (Delaware); Invalidity of U.S. Pat. No. 11,445,967 by U.S. Pat. No. 11,116,447 ("Yang"); Oct. 25, 2023; 14 pages.

Chart AA-1 Invalidity Contentions: U.S. Pat. No. 11,445,967; Case No. 22-351-CJB (Delaware); Invalidity of U.S. Pat. No. 11,445,967 by International Publication No. WO 2010/104952 to Mazar ("Mazar"); Oct. 25, 2023; 13 pages.

Chart A-10 Invalidity Contentions: U.S. Pat. No. 11,051,743; Case No. 22-351-CJB (Delaware); Invalidity of U.S. Pat. No. 11,051,743 by WO 2003/065926 ("Ozguz"); Oct. 25, 2023; 12 pages.

Chart A-9 Invalidity Contentions: U.S. Pat. No. 11,051,743; Case No. 22-351-CJB (Delaware); Invalidity of U.S. Pat. No. 11,051,743 by U.S. Pat. Pub. No. 2011/0009729 ("Shin"); Oct. 25, 2023; 12 pages.

Chart A-8 Invalidity Contentions: U.S. Pat. No. 11,051,743; Case No. 22-351-CJB (Delaware); Invalidity of U.S. Pat. No. 11,051,743 by WO 2008/005015 ("Shennib"); Oct. 25, 2023; 12 pages.

Chart A-7 Invalidity Contentions: U.S. Pat. No. 11,051,743; Case No. 22-351-CJB (Delaware); Invalidity of U.S. Pat. No. 11,051,743 by U.S. Pat. No. 7,206,630 ("Tarler"); Oct. 25, 2023; 12 pages.

Chart A-6 Invalidity Contentions: U.S. Pat. No. 11,051,743; Case No. 22-351-CJB (Delaware); Invalidity of U.S. Pat. No. 11,051,743 by U.S. Pat. No. 9,669,212 ("Mueller"); Oct. 25, 2023; 11 pages.

Chart A-5 Invalidity Contentions: U.S. Pat. No. 11,051,743; Case No. 22-351-CJB (Delaware); Invalidity of U.S. Pat. No. 11,051,743 by U.S. Pat. No. 10,413,251 ("Golda"); Oct. 25, 2023; 11 pages.

Chart A-4 Invalidity Contentions: U.S. Pat. No. 11,051,743; Case No. 22-351-CJB (Delaware); Invalidity of U.S. Pat. No. 11,051,743 by U.S. Pat. Pub. No. 2011/0077497 ("Oster"); Oct. 25, 2023; 11 pages.

Chart A-3 Invalidity Contentions: U.S. Pat. No. 11,051,743; Case No. 22-351-CJB (Delaware); Invalidity of U.S. Pat. No. 11,051,743 by U.S. Pat. No. 10,327,660 ("Gallego"); Oct. 25, 2023; 12 pages.

Chart A-2 Invalidity Contentions: U.S. Pat. No. 11,051,743; Case No. 22-351-CJB (Delaware); Invalidity of U.S. Pat. No. 11,051,743 by U.S. Pat. No. 11,116,447 ("Yang"); Oct. 25, 2023; 19 pages.

Chart A-1 Invalidity Contentions: U.S. Pat. No. 11,051,743; Case No. 22-351-CJB (Delaware); Invalidity of U.S. Pat. No. 11,051,743 by International Publication No. WO 2010/104952 to Mazar ("Mazar"); Oct. 25, 2023; 19 pages.

*Bardy Diagnostics, Inc.*, Plaintiff v. *Vital Connect, Inc.*; The United States District Court for the District of Delaware; C.A. No. 22-351 (CJB); Vitalconnect's Preliminary Invalidity Contentions; filed Oct. 25, 2023.

Wolf, "The Data-Driven Life," New York Times Magazine, Apr. 28, 2010, 13 pages.

Hill, "Adventures in Self-Surveillance: Fitbit, Tracking My Movement and Sleep," Forbes, Feb. 25, 2011, 11 pages.

Mehen, "Open health with the quantified self," Opensource.com, Aug. 25, 2011, 7 pages.

"23 Personal Tools to Learn More About Yourself," Flowingdata. com, Sep. 18, 2008, 18 pages.

Puurtinen et al., "Estimation of ECG Signal of closely separated bipolar electrodes using thorax models," Proceedings of the 26th Annual International Conference of the IEEE EMBS pp. 801-804, San Francisco, Calif., USA, Sep. 1-5, 2004, 4 pages.

Trägårdh et al., How many ECG leads do we need? Cardiol Clin. Aug. 2006;24(3):317-30, vii. doi: 10.1016/j. ccl.2006.04.005. PMID: 16939826; 14 pages.

Adams et al., U.S. Appl. No. 61/755,623, filed Jan. 23, 2013, 48 pages.

Toth et al., U.S. Appl. No. 61/832,131, filed Jun. 6, 2013, 82 pages.

Vishnubhotla, "Pre-processing of ECG signals for ambulatory use," Jan. 2009; 5 pages.

Chaimanonart et al., "A wireless batteryless in vivo EKG and body temperature sensing microsystem with adaptive RF powering for genetically engineered mice monitoring," Jul. 2009; 4 pages.

Alzaidi et al., "Smart Textiles Based Wireless ECG System," May 2012; 5 pages.

Saeed et al., "A Scalable Wireless Body Area Sensor Network for Health-Care Monitoring," Jun. 2009, 4 pages.

Pandian et al., "Wireless Sensor Network for Wearable Physiological Monitoring," Journal of Networks, vol. 3, No. 5, May 2008; 15 pages.

Mukala et al., "A Novel Zigbee-based Low-cost, Low-Power Wireless EKG system," IEEE, May 2010; 4 pages.

Aventyn, Inc., "Vital Connect, Aventyn Launch Wearable Biosensor Platform for Mobile Patient Monitoring", Dec. 12, 2013, 5 pages.

2nd Examination Report, EP Appln. No. 20 186 071.5-1113 mailed May 7, 2025.

* cited by examiner

13

12

12

12

30

30

60

<u>40</u>

100

CONFIGURABLE HARDWARE PLATFORM FOR PHYSIOLOGICAL MONITORING OF A LIVING BODY

PRIORITY CLAIM AND CROSS-REFERENCE TO RELATED APPLICATIONS

This continuation application claims priority to and the benefit of U.S. patent application Ser. No. 16/929,390 titled "CONFIGURABLE HARDWARE PLATFORM FOR PHYSIOLOGICAL MONITORING OF A LIVING BODY", filed Jul. 15, 2020, which claims priority under 35 U.S.C. § 119(e) to U.S. Provisional Patent App. No. 62/874,086, filed Jul. 15, 2019 and U.S. Provisional Patent App. No. 62/962,773, filed Jan. 17, 2020, the disclosures of which are incorporated by reference herein in their entirety and relied upon. U.S. patent application Ser. No. 16/929,390 is also a continuation-in-part of U.S. patent application Ser. No. 16/926,381, filed Jul. 10, 2020, which claims priority under 35 U.S.C. § 119(e) to U.S. Provisional Patent App. No. 62/873,754, filed Jul. 12, 2019, U.S. Provisional Patent App. No. 62/874,086, filed Jul. 15, 2019, U.S. Provisional Patent App. No. 62/873,740, filed Jul. 12, 10 2019, U.S. Provisional Patent App. No. 62/962,773, filed Jan. 17, 2020, and is further a continuation-in-part of U.S. patent application Ser. No. 16/919,626, filed on Jul. 2, 2020, which claims priority under 35 U.S.C. § 119(e) to U.S. Provisional Patent App. No. 62/870,506, filed Jul. 3, 2019, the disclosures of which are incorporated by reference.

FIELD

This application relates, in general, to health and medical apparatuses for sensing and recording the physiology of a living body and, in particular, to a configurable hardware platform for physiological monitoring of a living body.

BACKGROUND

Patient physiology is one of the four cornerstones of modern diagnostic medicine, which defines the structured process routinely employed by physicians and other medical professionals (henceforth, simply "physicians") to determine the nature and cause of patient health concerns and problems, and physicians need data on patient physiology that is timely, accurate, and reliable to provide effective health care. Through the diagnostic medicine process, a physician will make findings of possible diagnoses that can explain or match a patient's signs and symptoms in terms of a disease or medical condition, which thereby enables the physician to formulate a plan of treatment and follow-up care.

Medical diagnosis includes evaluating patient physiology, which describes the vital functions of the patient's anatomical structure, that is, the living body and its organs. A patient's physiology is determined through medical diagnostic procedures that include performing medical tests and, when available, reviewing patient data that has been collected through monitoring, although the data should first be correlated to patient symptoms to be of relevant diagnostic value.

Sporadic conditions present a special challenge because diagnostic tests performed in a physician's office may prove ineffective if the sporadic condition fails to present while the test is being performed. Sporadic conditions may be due to chronic or acute cause and can include transient signs, such as erratic heartbeat, muscle or nerve spasms, or hypoglycemia (or hyperglycemia) that may be accompanied by discernable symptoms. The unpredictable nature of sporadic conditions often makes the capturing of physiological data a matter of good timing. If the sporadic condition fails to occur during the course of a medical test, no physiological data, and therefore no diagnostic insight, is obtained.

In response, physicians have turned to ambulatory monitoring, which utilizes sensors placed cutaneously on or implanted within a patient's body that are attached to a recorder to provide physiological data capture while the patient goes about daily life. Ambulatory monitors include Holter monitors for electrocardiographic (ECG) monitoring, ambulatory blood pressure monitors (ABPM) for collecting blood pressure data at periodic intervals, and continuous glucose monitors that collect blood glucose data. Through ambulatory monitoring, physiological data may be captured and recorded continuously, upon demand for subsequent retrieval and evaluation, or might be recorded and reported in real or near real time, provided that the recorder is equipped with remote data communications capabilities using, for instance, cellular communications.

Ambulatory monitors that are either wholly implanted inside the patient's body or which use implanted sensors will generally provide cleaner physiological data relatively free of environmental noise and effects, especially when compared to data captured cutaneously. However, implantation is, by definition, invasive to some degree and carries more risk than cutaneous or external forms of ambulatory monitoring. Moreover, at least in part in light of the significance, complications, and expense of implantation, implanted forms of ambulatory monitors are also expected to be capable of operating over an extended period of time, so battery depletion must be considered to ensure sufficient service life. Thus, continuous recording of every heartbeat is not possible in conventional implantable ambulatory monitors due to power consumption and hard limits of onboard processing and storage, as continuous per-heartbeat monitoring places significant demands on these resources, which are strictly limited in an implantable device.

Typically, implanted forms of ambulatory monitors provide a single form of sensing into a patient's body using purpose-built hardware that will serve over the lifetime of the device, such as electrocardiographic electrodes. The associated recorder is similarly deployed to capture physiology through the sensing hardware by operating under a programming set that must accommodate an entire potential patient population. In some cases, additional programming complexity may be required to cover a minority of patients that nevertheless must be included in the programming set, albeit at the expense of conceivably dominating an engineering solution by requiring additional storage and computational resources.

Moreover, in conflict with the decision to provide a single form of sensing, an ambulatory monitoring environment is not static. A patient's body could (and likely will) change over time during the course of treatment, necessitating a different monitoring strategy or type of sensor for other forms of physiology. Notwithstanding, physicians are effectively limited to the hardware on-hand at the time of implanting. Such design tradeoffs, such as having only a single form of sensing and reliance upon a general purpose programming set, limit the abilities of implanted forms of conventional ambulatory monitors. New sensory capabilities cannot be added without implanting new sensing hardware, plus each new sensor must somehow be interfaced to the recorder, which will need to be able to handle the new sensor in terms of data capture, processing, and storage.

Additional sensory capabilities may also adversely effect battery life, which can be of particular concern if the recorder lacks recharging capabilities and the intended service life of the implantable device could be negatively impacted.

Therefore, a need remains for an implanted form of ambulatory physiological monitor that offers per-heartbeat monitoring with flexible and extensible monitoring capabilities in terms of sensory capabilities, scope of device programming, and service life, without having to implant additional hardware.

SUMMARY

A configurable hardware platform for health and medical monitoring of physiology is housed within a hermetically sealed implantable medical device (IMD). Physically, the IMD has a generally tubular shape that includes a central tubular body with rounded semi spherical end caps. When configured to measure electrocardiographic signals, the central tubular body and one of the semi spherical end caps function as electrode dipoles. The semi spherical end cap is electrically conductive yet electrically insulated from the central tubular body. As well, the outside surface of the central tubular body is partially electrically insulated, generally on the surface closest to the electrically conductive semi spherical end cap to form a non-electrically conductive inversion with only the outside surface distal to that semi spherical end cap being exposed.

When placed within the central tubular body, a flexible circuit board forms three aspects of a microcontroller circuit assembly that respectively define a receiving coil for inductive charging and optional communication, a high frequency antenna for radio frequency (RF) data exchange, and a flexible circuit board containing a microcontroller and device circuitry. An onboard power source that includes a rechargeable energy cell, battery, or supercapacitor is also placed within the tubular body to one end of the flexible circuit board and, optionally, in electrical contact through a protection circuit with the electrically conductive semi spherical end cap, thereby serving as an electrical feed-through to the flexible circuit board. The power source may be recharged through a charging and conditioning circuit interfaced with the microcontroller using a non-contact method, such as inductive charging, resonant charging, energy harvesting, thermal gradient charging, ultrasonic charging, RF-based charging or charging by ambient or driven motion.

The IMD can provide continuous monitoring of the patient on a heartbeat-by-heartbeat basis. The monitoring data is regularly offloaded through live transmission or delayed transmission, which may occur, for instance, two days or longer following recordation, or live monitoring. The offloaded monitoring data is analyzed at a datacenter, where the processing constraints imposed by the computational and resource limits of the IMD are not a hindrance. Additionally, the IMD is equipped with one or more physiological or non-physiological sensors that can be selectively activated over the implantation lifetime to tailor the monitoring of the patient to ongoing diagnostic needs. The physiological sensors non-exhaustively include ECG, temperature, oxygen saturation, respiration, blood glucose, and sensors which detect movement, position, or acceleration.

One embodiment provides an implantable medical device. A housing includes a hollow body forming a first electrode on an outer surface with end caps affixed to opposite ends, one such end cap forming a second electrode on an outer surface. A microcontroller circuit is provided circumferentially within the housing and includes a microcontroller operable under program instructions stored within a non-volatile memory device. An analog front end is electrically interfaced to the first and the second electrodes and is operable to sense electrocardiographic signals. A transceiver circuit is operable to wirelessly communicate with an external data device. The program instructions define instructions for the microcontroller to continuously sample the electrocardiographic signals into the non-volatile memory device and to offload the non-volatile memory device to the external data device via the transceiver circuit. A receiving coil and a charging circuit are operable to charge an onboard power source for the microcontroller circuit.

Another embodiment provides an implantable medical device. A cylindrical hollow body forms a first electrode on an outer surface. A first spherical end cap is attached on one end of the hollow body. A second spherical end cap is attached on another end of the hollow body and forms a second electrode on an outer surface. Electronic circuitry is housed within the hollow body. A microcontroller is operable under program instructions contained in microcode stored within a non-volatile memory device. A physiological sensor is operable to sense physiological data and is electrically interfaced to the microcontroller. An analog front end is electrically interfaced to the first and the second electrodes and the microcontroller and operable to sense electrocardiographic signals. A transceiver circuit is electrically interfaced to a high frequency antenna housed within the second spherical end cap and the microcontroller and is operable to wirelessly communicate with an external data device. A receiving coil is formed as part of a non-contact charging circuit. The program instructions are operable to instruct the microcontroller to continuously sample the electrocardiographic signals and the physiological data at set times into the non-volatile memory device and to offload the non-volatile memory device to the external data device via the transceiver circuit. A power source is housed within the hollow body and is electrically interfaced to the non-contact charging circuit. The power source is operable to power the microcontroller.

Yet another embodiment provides an implantable medical device. A main cylindrical body defines an axial bore extending longitudinally over the length of the main cylindrical body and exposes an electrically conductive area defining a first electrode on at least part of the outer surface of the main cylindrical body. A protective spherical end cap is fixedly disposed on one end of the main cylindrical body and defines an interior cavity. The protective spherical end cap further exposes an electrically conductive area defining a second electrode on at least part of the outer surface of the protective spherical end cap. An antenna spherical end cap is fixedly disposed on one end of the main cylindrical body and defines an interior cavity with a high frequency antenna housed within. A printed circuit board is housed within the main cylindrical body. Electronic circuitry includes a physiological sensor operable to sense physiological data. The electronic circuitry also includes an analog front end electrically interfaced to the first and the second electrodes and operable to sense electrocardiographic signals. A transceiver circuit is electrically interfaced to the high frequency antenna and is operable to wirelessly communicate with an external data device. A microcontroller is operable under program instructions contained in microcode stored within a non-volatile memory device and is electrically interfaced with a physiological sensor, the analog front end, and the transceiver circuit. The microcontroller is operable under the program instructions to record the physiological data at set times and the electrocardiographic signals continuously into the non-volatile memory device and to offload the electrocardiographic signals from the non-volatile memory device to the external data device. A receiving coil is formed on an extended surface of the printed circuit board that is adapted to be circumferentially disposed about the electronic circuitry and is provided as part of a non-contact charging circuit. A power source comprising a rechargeable energy cell housed within the main cylindrical body and electrically interfaced with the charging circuit to power the electronic circuitry.

The configurable hardware platform provides several advantages over conventional designs, including rapid recharging, a flexible and extensible hardware platform, the ability to provide full and complete disclosure of physiological recording data (in contrast to binned, averaged, event-based or other forms of telemetric disclosure), continuous monitoring, store and forward functionality, and the ability to serve as an extended or lifetime monitor.

Still other embodiments will become readily apparent to those skilled in the art from the following detailed description, wherein are described embodiments by way of illustrating the best mode contemplated. As will be realized, other and different embodiments are possible, and the embodiments' several details are capable of modifications in various obvious respects, all without departing from their spirit and the scope. Accordingly, the drawings and detailed description are to be regarded as illustrative in nature and not as restrictive.

DETAILED DESCRIPTION

Related Applications

Figure 1:
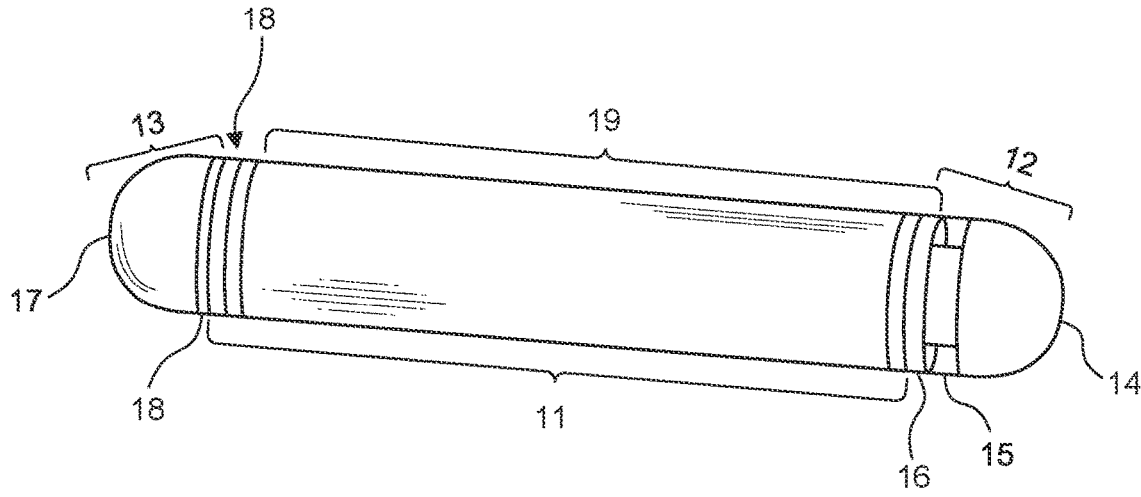
FIG. 1 is an outer perspective view showing an IMD that houses a configurable hardware platform for physiological monitoring of a living body in accordance with one embodiment.

This non-provisional patent application is related to in commonly-assigned U.S. Pat. No. 9,545,204, issued Jan. 17, 2017 to Bishay et al.; U.S. Pat. No. 9,730,593, issued Aug. 15, 2017 to Felix et al.; U.S. Pat. No. 9,717,432, issued Aug. 1, 2017 to Felix et al.; U.S. Pat. No. 9,775,536, issued Oct. 3, 2017 to Felix et al.; U.S. Pat. No. 9,433,380, issued Sep. 6, 2016 to Bishay et al.; U.S. Pat. No. 9,655,538, issued May 23, 2017 to Felix et al.; U.S. Pat. No. 9,364,155, issued Jun. 14, 2016 to Bardy et al.; U.S. Pat. No. 9,737,224, issued Aug. 22, 2017 to Bardy et al.; U.S. Pat. No. 9,433,367, issued Sep. 6, 2016 to Felix et al.; U.S. Pat. No. 9,700,227, issued Jul. 11, 2017 to Bishay et al.; U.S. Pat. No. 9,717,433, issued Aug. 1, 2017 to Felix et al.; U.S. Pat. No. 9,615,763, issued Apr. 11, 2017 to Felix et al.; U.S. Pat. No. 9,642,537, issued May 9, 2017 to Felix et al.; U.S. Pat. No. 9,408,545, issued Aug. 9, 2016 to Felix et al.; U.S. Pat. No. 9,655,537, issued May 23, 2017 to Bardy et al.; U.S. Pat. No. 10,165, 946, issued Jan. 1, 2019 to Bardy et al.; U.S. Pat. No. 10,433,748, issued Oct. 8, 2019, to Bishay et al.; U.S. Pat. No. 10,667,711, issued Jun. 2, 2020, to Felix et al.; U.S. Pat. No. 9,619,660, issued Apr. 11, 2017 to Felix et al.; U.S. Pat. No. 10,463,269, issued Nov. 5, 2019 to Boleyn et al.; U.S. Pat. No. 9,408,551, issued Aug. 9, 2016 to Bardy et al.; U.S. Patent Application Publication No. 2019/0069800, published Mar. 7, 2019 to Bardy et al.; U.S. Patent Application Publication No. 2019/0069798, published Mar. 7, 2019 to Bardy et al.; U.S. Patent Application Publication No. 2019/ 0117099, published Apr. 25, 2019 to Bardy et al.; U.S. Patent Application Publication No. 2019/0099105, published Apr. 4, 2019 to Felix et al.; U.S. Pat. No. 10,624,551, issued Apr. 21, 2020 to Bardy et al.; U.S. Pat. No. 10,251, 576, issued Apr. 9, 2019 to Bardy et al.; U.S. Pat. No. 9,345,414, issued May 24, 2016 to Bardy et al.; U.S. Pat. No. 10,433,751, issued Oct. 8, 2019 to Bardy et al.; U.S. Pat. No. 9,504,423, issued Nov. 29, 2016 to Bardy et al.; U.S. Patent Application Publication No. 2019/0167139, published Jun. 6, 2019 to Bardy et al.; U.S. Design Pat. No. D717955, issued Nov. 18, 2014 to Bishay et al.; U.S. Design Pat. No. D744659, issued Dec. 1, 2015 to Bishay et al.; U.S. Design Pat. No. D838370, issued Jan. 15, 2019 to Bardy et al.; U.S. Design Pat. No. D801528, issued Oct. 31, 2017 to Bardy et al.; U.S. Design Patent No. D766447, issued Sep. 13, 2016 to Bishay et al.; U.S. Design Patent No. D793566, issued Aug. 1, 2017 to Bishay et al.; U.S. Design Pat. No. D831833, issued Oct. 23, 2018 to Bishay et al.; and U.S. Design Patent Application Ser. No. 29/612,334, entitled: "Extended Wear Electrode Patch," filed Jul. 31, 2017, pending; U.S. patent application Ser. No. 16/919,626, filed on Jul. 2, 2020, entitled "Subcutaneous P-Wave Centric Insertable Cardiac Monitor With Energy Harvesting Capabilities," pending; and U.S. patent application Ser. No. 16/926,381, filed Jul. 10, 2020, entitled "System and Method for Remote ECG Data Streaming in Real-Time," pending, the disclosures of which are incorporated by reference.

OVERVIEW

A configurable hardware platform for health and medical monitoring of physiology is housed within a hermetically sealed, implantable medical device (IMD). The IMD provides an implanted form of ambulatory physiological monitor that offers per-heartbeat monitoring with flexible and extensible monitoring capabilities. The IMD is designed to be implanted within a living body and to operate over an extended time period while monitoring different types of patient physiology, possibly at different times and in different ways.

The IMD can record every heartbeat, perform live transmission or delayed transmission, which may occur, for instance, two days or longer following recordation, or live monitoring. When every heartbeat is recorded and sent, the platform does not require an analysis algorithm onboard; rather, the analysis algorithm could be implemented at a datacenter or on a cell phone to do the heavy data processing by utilizing the better computing resources available on those platforms. The IMD is equipped with one or more physiological sensors that non-exhaustively include ECG, temperature, pulse oximetry, oxygen saturation, respiration, blood glucose, blood pressure, and drug levels or any appropriate measure of disease. In a further embodiment, the IMD can also monitor non-physiological data when the IMD is equipped with an appropriate type of sensor, such as posture as derived from data measured by an actigraphy sensor, accelerometer or inertial motion sensor. Other types of sensors and forms of physiology and non-physiological data capture are possible, such as cardiac effort level, thoracic impedance, and sound recording, including ultrasonic and sub-sonic sound recording.

The degree of surgical invasiveness required to implant the IMD depends upon the intended situs within the body, which is at least in part dictated by the desired range of physiology to be monitored. For instance, electrocardiographic monitoring of the heart that emphasizes the propagation of low amplitude, relatively low frequency content cardiac action potentials, particularly the P-waves that are generated during atrial activation, can be efficaciously performed by implanting the IMD in a subcutaneous situs located axially and slightly to either the left or right of the sternal midline in the parasternal region of the chest. This type of subcutaneous implantation can be performed in a physician's office using a specialized implantation instrument that includes a trocar to incise the skin and form a subcutaneous tunnel, and a cannula through which the IMD is guided into place, after which the implantation instrument is withdrawn and the surgical incision is closed.

Specific details of the IMD's housing, electronic and support circuitry, power source, and microarchitecture will now be discussed.

Housing

Physically, the IMD has a generally cylindrical shape that includes a central tubular body with rounded semi spherical end caps, although other shapes and configurations are possible. In a further embodiment, one or both of the semi spherical end caps may be replaced pointed or semi-pointed tips to ease insertion into the body. FIG. 1 is an outer perspective view showing an IMD 10 that houses a configurable hardware platform for physiological monitoring of a living body in accordance with one embodiment. The IMD 10 includes three primary assemblies. The main middle section of the IMD 10 is a central body 11 that can be formed from a medical grade titanium or similar medical implantation-safe material. The central body 11 has a tubular or cylindrical shape that defines an axial bore, which provides a hollow interior cavity that is open on both end caps running longitudinally over the length of the central body 11. Other shapes having non-circular or non-spherical shapes are possible. Rounded semi spherical end caps 12 and 13 are welded or affixed to the central body 11 to form a hermetically sealed device housing. The end caps 12 and 13 can be formed in other shapes, such as pointed or semi-pointed tips.

The central body 11 houses a flexible circuit board, a low frequency resonant charger antenna to facilitate device recharging, and an onboard power source generally consisting of a rechargeable energy cell, battery, or supercapacitor. One of the semi spherical end caps, known as the "Protectrode" 12, serves a dual purpose as an electrode and housing for patient and device protection components. The other semi spherical end cap, known as the "Radome" 13, houses a high frequency antenna used for transmitting data over an RF link, using, for instance, Bluetooth or WiFi. Additionally, the "Radome" 13 could be used to house an inductive antenna and inductive link. The RF link may also be used for device calibration and configuration. In a further embodiment, the "Radome" 13 can also house physiological sensors, such as pulse oximetry and blood pressure. In a further embodiment, the optically clear "Radome" 13 may allow light or other forms of radiation to be received and transmitted through to passively facilitate collection of other vital signs, such as pulse oximetry and blood pressure. In a still further embodiment, fiber optics or lenses implanted into the "Radome" 13 may facilitate collection of vital signs by sensors housed elsewhere.

The IMD 10 has an overall length of approximately 5.5 cm to 8.5 cm with an outer diameter, measured across the central body 11, of approximately 5-8 mm and a wall thickness of approximately 0.3 mm; however, other dimensions, including overall length, wall thickness, and outer diameter, are possible depending upon both the electronic circuitry and power source that need to be housed within and the types and numbers of physiological and non-physiological sensors.

In a further embodiment, the IMD 10 can be filled with a gas, such as argon or other inert gas. In particular, argon gas is conventionally used when welding titanium components and, when oxygen-purged into the interior of the IMD 10, further serves to preserve the electrical components and facilitate device longevity. In addition, supporting structure, such as an acrylic rod, can be used as an internal spacer to help keep the internal components in proper position.

In one embodiment, the central body 11 and the "Protectrode" 12 can be micro bead blasted to respectively increase the roughness of the central body 11 to improve silicone or Parylene bonding and to increase the surface area of the "Protectrode" 12 for better signal quality. A titanium nitride coating could also be applied to dramatically increase the surface area of the device.

The conductive surface 18 is formed by partially insulating the outside surface of the central body 11 using a non-electrically conductive, insulating surface treatment or coating ("insulating coating") 19. The insulating coating 19 is generally applied on the outer surface closest to the "Protectrode" 12, which maximizes the electrode dipole spacing. In one embodiment, the insulating coating 19 can be a chemical vapor deposited poly polymer, such as Parylene C. In a further embodiment, the insulating coating 19 can be a silicone polymer-based (polysiloxanes) coating. Alternatively, both forms of coatings, poly polymer and silicone polymer, could be employed. Poly polymers exhibit superior moisture resistance and insulation resistance properties, but are susceptible to damage from scratches and scrapes. Silicone polymer coatings form a durable protective layer and, when applied over a poly polymer coating, such as Parylene C, can protect the underlying coating from scratches and scrapes during insertion, repositioning, or removal of the IMD 10.

The end 22 of the central body 11 closest to the conductive surface 18 interfaces to the "Radome" 13. In one embodiment, the high frequency antenna is a separate component that is contained within the "Radome" 13. Here, the high frequency antenna can be held in place by filling the cavity of the "Radome" 13 with a filler material, such as acrylic, urethane, glass, or similar material, and the high frequency antennal is interfaced to a flexible circuit board via an electrical contact 20 that can be soldered or bonded to the high frequency antenna. In a further embodiment, the high frequency antenna is formed on a foldable "ear" section of the flexible circuit board and routed into the "Radome" 13 assembly.

Figure 2:
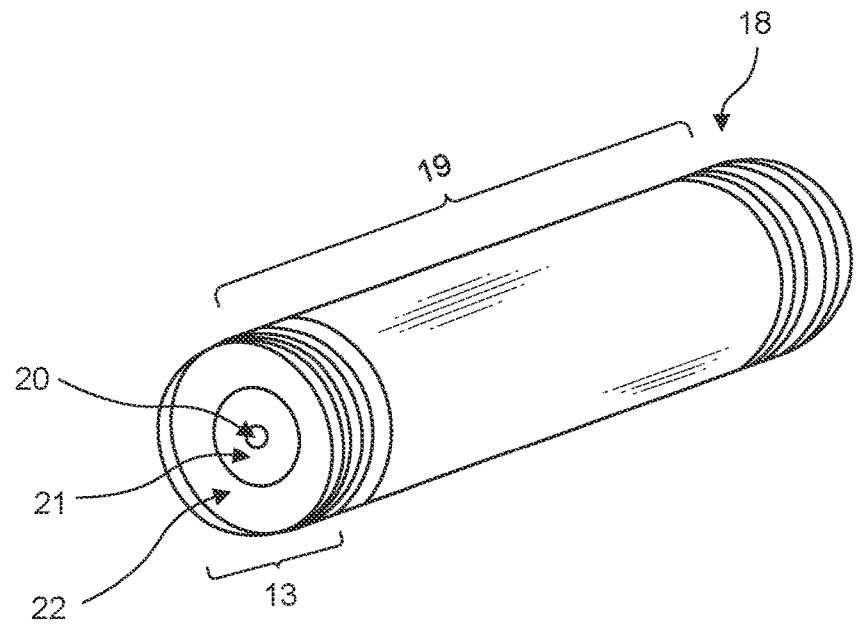
FIG. 2 is an outer perspective view showing the central tubular body of the IMD of FIG. 1.

In one embodiment, when configured to measure electrocardiographic signals, the "Protectrode" 12 and an exposed, conductive surface 18 of the central body 11 function as an electrode dipole. Other forms of electrode dipoles are possible. FIG. 2 is an outer perspective view showing the central body 11 of the IMD 10 of FIG. 1. The end cap 14 of the "Protectrode" 12 forms one electrode. An exposed, conductive surface 18 of the central body 11 distal to the "Protectrode" 12 forms the other electrode. The metallic case of the power source provides an electrical feedthrough from the "Protectrode" 12 to a flexible circuit board, thereby simplifying construction.

"Radome"

Figure 3:
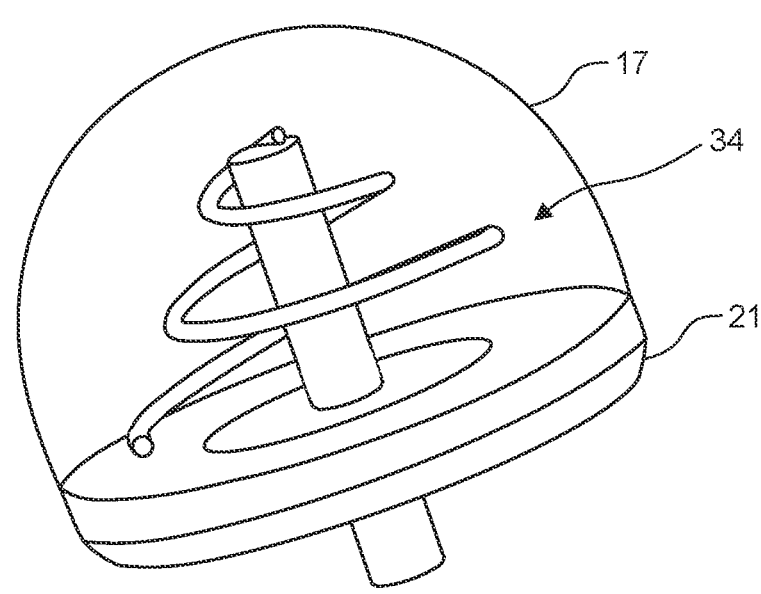
FIG. 3 is a side perspective view showing the semi spherical end cap ("Radome") of the IMD of FIG. 1.

Informally, the non-electrically conductive semi spherical end cap forms a "Radome" (radar dome) 13 that serves as a housing for a high frequency antenna used for RF data exchange. FIG. 3 is a side perspective view showing the semi spherical end cap ("Radome") of the IMD 10 of FIG. 1. A high frequency antenna 34 for data exchange is housed within the "Radome" 13. Note that more than one high frequency antenna could be included. The "Radome" 13 is an assembly that includes an electrically insulated semi sphere 17 formed from a medical implantation-safe grade material, such as acrylic, glass, ruby crystal, or ceramic, and a metallic weld ring 21 formed from a medical grade titanium or similar medical implantation-safe metal. These parts are bonded together using pressure fitting, brazing, laser welding, or electron beam welding. In a further embodiment, the high frequency antenna is defined as part of a flexible circuit board or folded metal shape, folded wire, or other similar structure, as further described infra.

"Protectrode"

Figure 4:
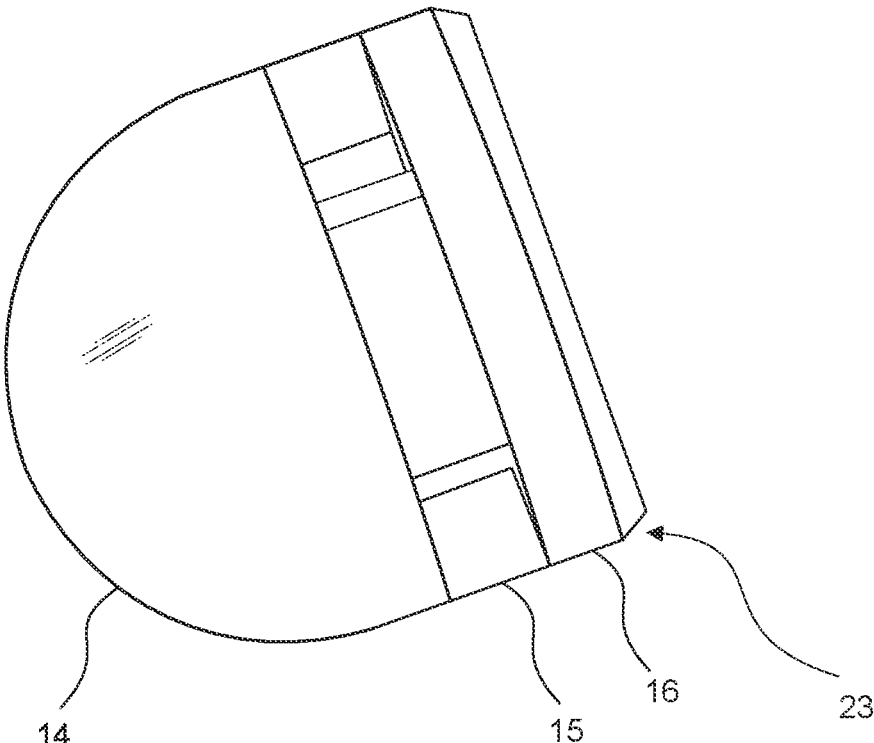
FIG. 4 is a side perspective view showing the electrically conductive semi spherical end cap ("Protectrode") of the IMD of FIG. 1.

Informally, the electrically conductive semi spherical end cap forms a "Protectrode" (feeder electrode) 12 that serves a dual purpose as an electrode and as housing for patient and device protection components. FIG. 4 is a side perspective view showing the electrically conductive semi spherical end cap ("Protectrode") of the IMD 10 of FIG. 1. The "Protectrode" 12 is an assembly that includes an electrically conductive semi sphere 14 formed from a medical grade titanium or similar medical implantation-safe conductor, an insulator ring 15 formed from a medical implantation-safe grade material, such as acrylic, glass, ruby crystal, or ceramic, and a metallic weld ring 16, which can include a chamfered edge 23 to facilitate welding to the central body 11, formed from a medical grade titanium or similar medical implantation-safe metal. These parts are bonded together with heat fitting, press fitting, brazing, epoxy adhesive, silicon adhesive or other similar bonding agent.

Figure 5:
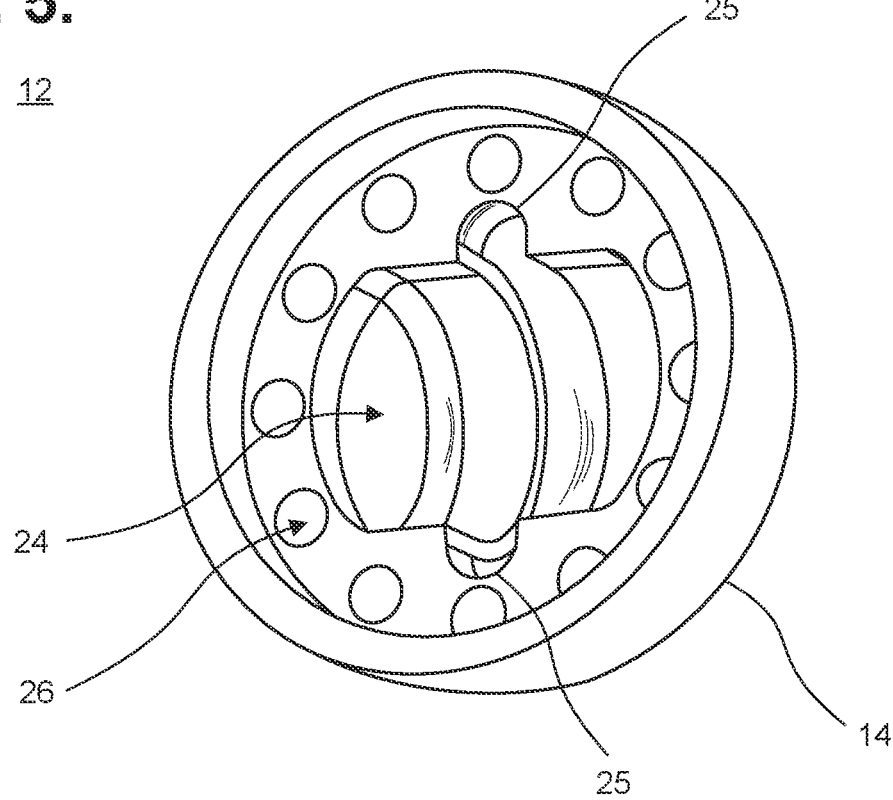
FIG. 5 is an inside perspective view showing the interior of the end cap of the "Protectrode" of FIG. 4.
Figure 6:
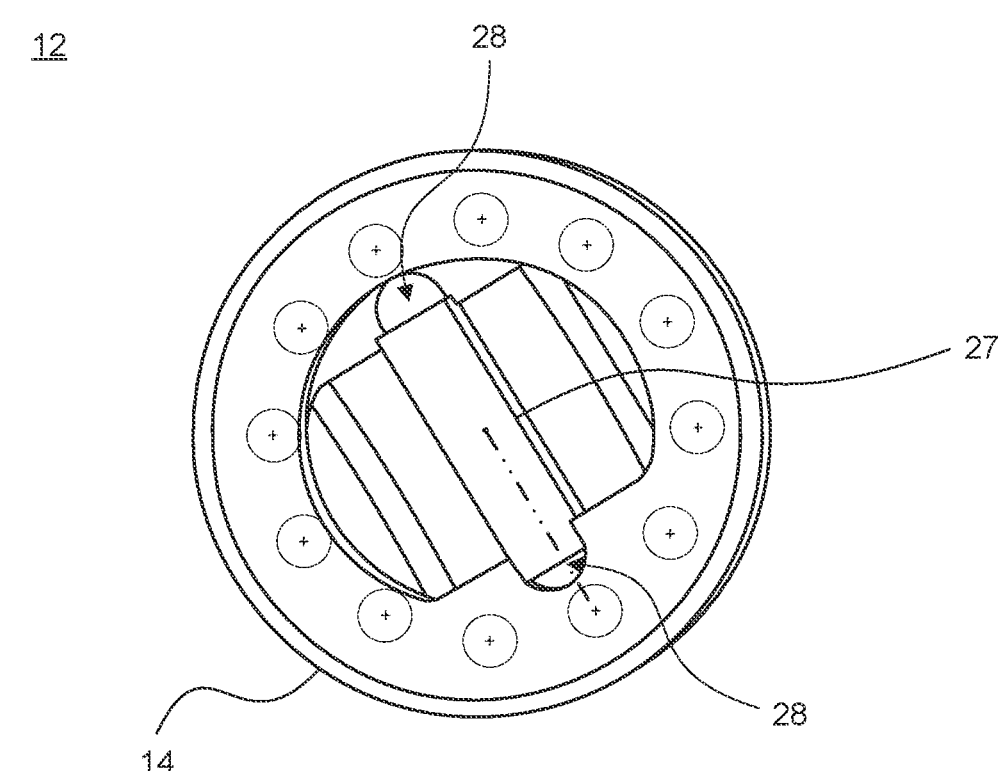
FIG. 6 is an inside perspective view showing the interior of the end cap of the "Protectrode" of FIG. 4.

The construction details of the "Protectrode" 12 will now be discussed. FIG. 5 is an inside perspective view showing the interior of the end cap 14 of the "Protectrode" 12 of FIG. 4. In one embodiment, a set of concave dimples 26 is formed along an inside shelf surface of the end cap 14. The dimples 26 increase surface area and thereby facilitate adhesion of the end cap 14 to the insulator ring 15, they also resist circular rotation. FIG. 6 is an inside perspective view showing the interior of the end cap 14 of the "Protectrode" 12 of FIG. 4. A circumferential groove 25 is longitudinally defined within a cavity 24 inside the end cap 14. The groove 25 provides a mounting location for a circuit board 27. The edges of the circuit board 27 are plated with a set of electrically conductive coatings 28 that include, starting from the circuit board 27 and proceeding outward, copper, nickel (thickly applied), palladium (thinly applied), and gold (of medium thickness), although other materials and combinations of layers are possible. The conductive coatings 28 are necessary to ensure against a galvanic reaction between the copper traces of the circuit board 27 and the titanium shell of the end cap 14. The "Protectrode" may be filled with epoxy or a similar material such as silicon to increase strength and dielectric breakdown properties and provide resistance to corrosion. The filler also will bond with the insulator when the insulator is made out of a brittle material such as ruby, glass or ceramic. The adhesive will hold in place the brittle material should the material fracture during an extreme impact event, such as a car crash.

Figure 7:
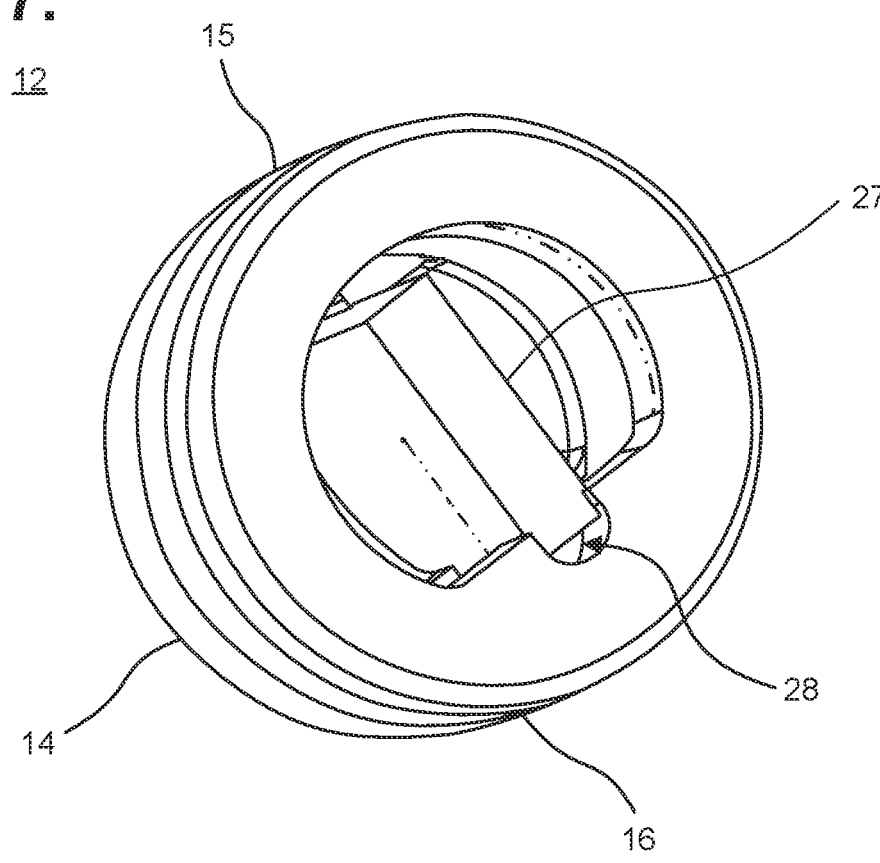
FIG. 7 is an inside perspective view showing the interior of the fully assembled "Protectrode" of FIG. 4.

FIG. 7 is an inside perspective view showing the interior of the fully assembled "Protectrode" 12 of FIG. 4. The edges of the circuit board 27 contact the "Protectrode" 12 along the groove 25. The edges of the circuit board 27 contact the "Protectrode" 12 in two places, in the groove 25 along the end cap 14 and in the groove 25 along the metallic weld ring 16 (the groove 25 is formed along only one side of the metallic weld ring 16, but could be formed along both sides).

Figure 8:
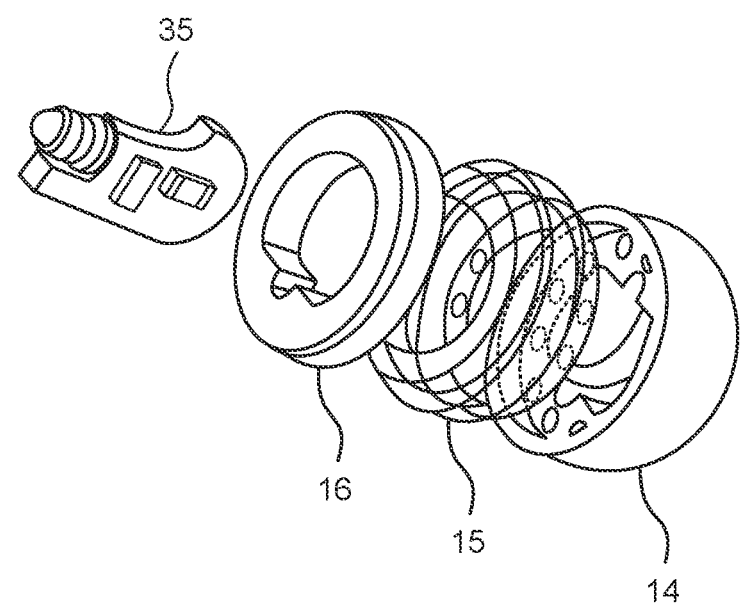
FIG. 8 is an exploded perspective view showing the components of the "Protectrode" of FIG. 4.

FIG. 8 is an exploded perspective view showing the components of the "Protectrode" of FIG. 4. The circuit board 27 includes a protection circuit 35 for the electrode dipole. The insulator ring 15 electrically isolates these two contact points, thereby allowing the protection circuit 35 to interface with both electrodes, that is, the "Protectrode" 12 and the conductive surface 18.

Flexible Circuit Board

The primary electrical structure of the IMD 10 is made out of a single flexible circuit board, which effectively eliminates many inter-circuit board connections and the delicate construction required to create them.

Folded Shape

Figure 9:
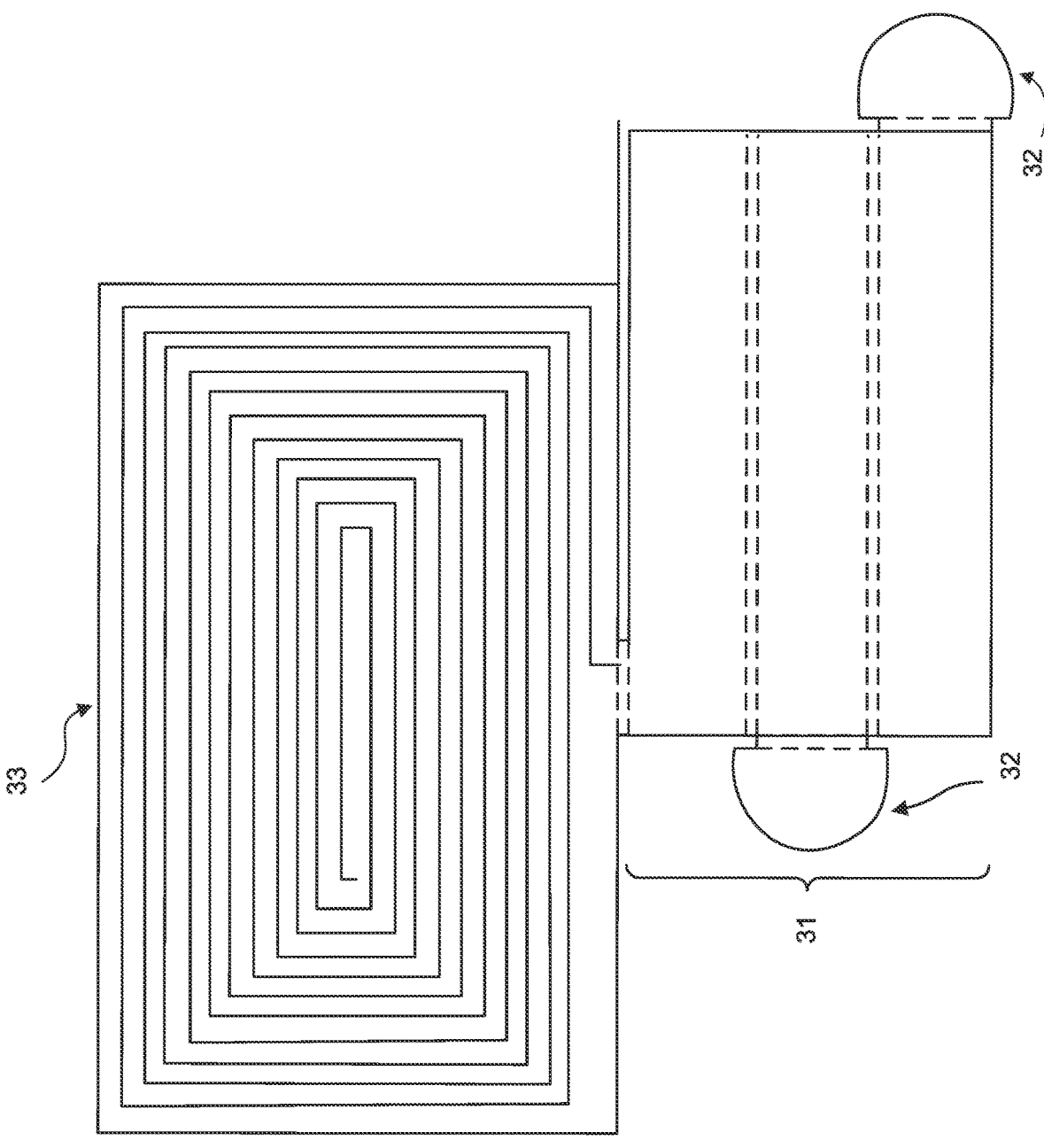
FIG. 9 is a top plan view of a flexible circuit board for use in the IMD of FIG. 1 in a flat, unfolded form.

The flexible circuit board 30 resembles a piece of origami paper that is folded into final shape, which is expected to increase device longevity and reliability by simplifying the design and eliminate the commonly-encountered failure points found in traditional designs. FIG. 9 is a top plan view of a flexible circuit board 30 for use in the IMD 10 of FIG. 1 in a flat, unfolded form. The flexible circuit board 30 is formed out of a single piece of flexible circuit board substrate defining a flexible circuit board 30 for placement of the microcontroller and device circuitry, a pair of vertically disposed foldable "ears" 32 provided on opposite ends of the flexible circuit board 30, and a foldable (or rollable) area 33 that acts as a receiving coil for inductive power coupling. On one end of the flexible circuit board 30, a foldable ear 32 connects to a power source and the feedthrough provided by the power source's case. On the other end of the flexible circuit board 30, the foldable ear 32 either connects to a high frequency antenna that is a separate component contained within the "Radome" 13 or the foldable ear 32 itself forms the high frequency antenna 23. The flexible circuit board 30 can include circuit traces on all sides, or multiple layers covered by an insulating layers to maximize space utilization. In one embodiment, the receiving coil's circuit traces are copper, although other types of conductive materials could be used.

Figure 10:
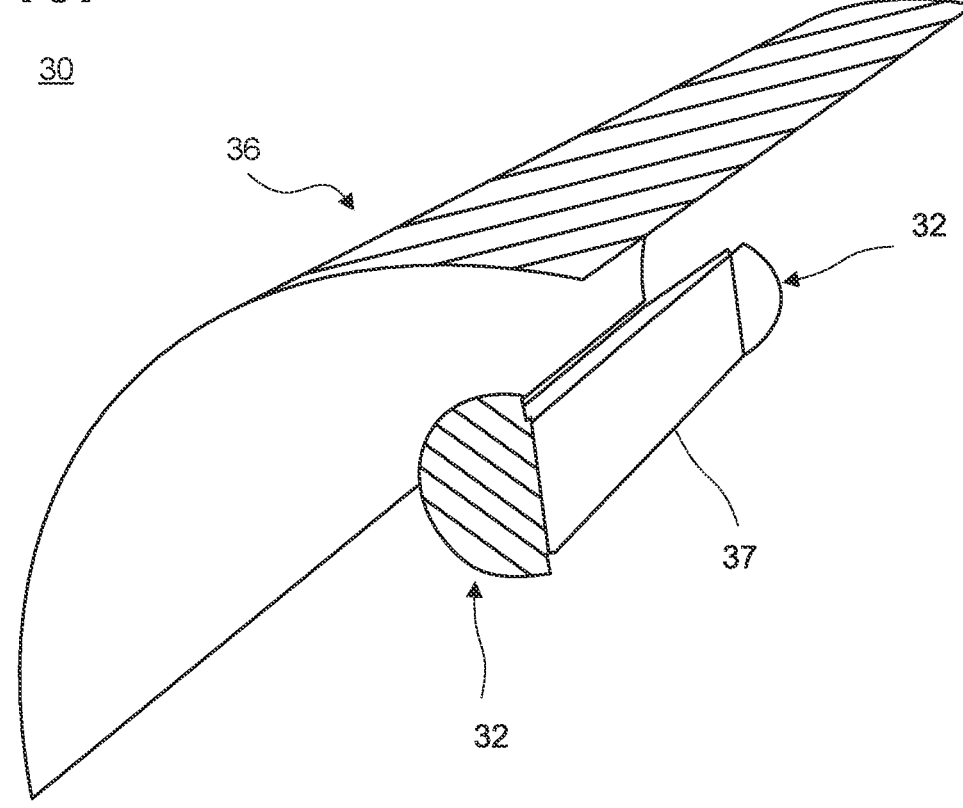
FIG. 10 is a three-quarters perspective view of the flexible circuit board of FIG. 9 in a semi-folded configuration.

FIG. 10 is a three-quarters perspective view of the flexible circuit board of FIG. 9 in a semi-folded configuration. When placed within the central tubular body, the flexible circuit board 30 forms three aspects 31 of a microcontroller circuit assembly that respectively define a receiving coil 36 for energy capture, a pair of inter-device connecting ears 32, and a printed circuit board 37 containing a low power micro-controller and device circuitry operable to execute under modular micro program control as specified in firmware. The flexible circuit board 30 can be folded into a triangular shape or horseshoe shape (not shown) and each of the inter-device connecting ears 32 are folded angularly inward towards the triangular ends of the triangular shape 34. The foldable area 33 is either folded or rolled around the triangular shape of the flexible circuit board 30 and ears 32. Other shapes may be possible, including other variations on "ears" or extensions to the flexible circuit board 30.

Receiving Coil

A power receiving coil 36 is formed by folding (or rolling) the foldable (or rollable) area 33 (shown in FIG. 9) circumferentially about the triangular or horseshoe shape that contains the microcontroller and device circuitry. The foldable (or rollable) area 33, however, is longer than the flexible circuit board 30 and is defined, when installed inside the IMD 10, to extend for substantially the entire longitudinal length of the tubular body 11. The receiving coil 36 uses planar trace construction to maximize the capture of magnetic flux and provides insulation between the positive and negative electrode poles of the IMD 10. In further embodiments, signals can be routed from the spherical end caps through the antenna. As well, additional sensors can be implanted in the antennas.

In one embodiment, the receiving coil 36 that is used for gathering energy to recharge the power source is connected to a clamping diode array and fusible link. In the presence of extreme electromagnetic environments, the protection diode array will limit the voltage across the antenna protecting the device charging circuitry. If the diode array is overwhelmed for a long enough period of time, the fusible link will open to protect the patient from the effects of device heating due to excessive charging energy received from the receiving coil. The fusible link may optionally be constructed out of a resettable overcurrent device, thermally actuated device, or fusible current limiting device.

In a further embodiment, the foldable (or rollable) area 33 is defined to form, when installed inside the IMD 10, a diagonal antenna that (not shown) will limit dead zones by creating a spiral where the two halves of the receiving coil connect. A standard square-shaped receiving coil could potentially lead to an RF dead zone in certain orientations. The diagonal antenna has a wide track and is overlaid, so that there are two overlapping areas, which should result in efficient flux capture for fields passing through the antenna.

In one embodiment, the high frequency antenna, when formed on a foldable ear 32 of the flexible circuit board 30, can be folded in different ways to create a range of antenna shapes. Note that more than one high frequency antenna could be used. The antenna is completely integrated into the flex circuit, which eliminates feedthrough that also translates into much better energy coupling.

In one embodiment, the receiving coil is sandwiched between the central tubular body 11, which can be a titanium cylindrical enclosure, and the case of the power source, described infra, which can also be a cylindrical titanium battery case. During inductive charging, eddy currents are induced in the titanium battery case. The eddy currents can raise the temperature of the IMD 10 and can reduce charge efficiency. This effect can be countered by reflecting the low frequency charging magnetic field into the low frequency energy receiving antenna with the increase in efficiency resulting in less heating. A ferrite coating or ferrite sheet can be applied to the outside casing of the power source to increase charge transfer efficiency by reflecting energy back into the receiving coil. Since the energy is reflected, less heating of the power source will occur during inductive charging due to decreased eddy currents.

Forming the power receiving coil 36 by folding or rolling the flexible circuit board provides several benefits over conventional implantable device design. First, the folding or rolling of the flexible circuit board affords a thin design that facilitates patient comfort by enabling compact packaging, resulting in an smaller device than would otherwise be available in a comparably rechargeable design. Second, the wide aspect ratio of the power receiving coil, when compared with to a traditional wire coil, allows a low loss element, thereby decreasing device heating. Moreover, the low loss element enables quicker charging through higher energy reception without excessive heating. Third, the unique shape enables injectable implantation technique that are not possible with traditional planar coils. Finally, the completely integrated design of the printed circuit board containing the microcontroller and related circuitry and the receiving coil simplifies device design, decreases weight, improves device longevity, and increases patient safety by virtue of requiring fewer parts and no discrete interconnections using, for instance, soldered wires or circuit traces.

Power Source and Charging Circuit

A power source that includes an inductively-rechargeable energy cell, battery, or supercapacitor is also placed within the IMD 10 to one end of the flexible circuit board 30 and in electrical contact with the electrically conductive semi spherical end cap 13, thereby serving as an electrical feed-through to the flexible circuit board 30. The power source may be recharged through a charging and conditioning circuit interfaced with the microcontroller using a non-contact method, such as inductive charging, resonant charging, energy harvesting, thermal gradient charging, ultrasonic charging, RF-based charging or charging by ambient or driven motion including vibration. Low frequency charging circuits are most efficient at transmitting energy through solid objects. When a charging circuit operates, vibrations are induced in the coils used in the charger as well as surrounding conductive objects. However, these vibrations, if within the human audible hearing range (or a close multiple thereof) create sound.

A traditional charging circuit uses a single frequency to transmit power. If the frequency or a major harmonic thereof is within the audible human hearing range, a single tone that humans can find very annoying could result. To overcome this issue, traditional charging circuits operate above the human audible hearing range. However, instead of using a single frequency for charging, a low frequency charging circuit could also modulate the charging waveform at audible frequencies that result in a pleasant sound for the user, so as to allow the technical benefits of low frequency charging without causing annoyance to humans.

Modulation of frequencies requires receive and transmit circuitry with higher bandwidth to accommodate the frequency shifts efficiently. The modulation can cause decreased circuit Q ("quality"), which can be overcome by using a variable capacitor or other automatic tuning circuit to ensure sufficient resonance as the frequency changes. For example, if the frequency changes, tuning may be required to restore satisfactory coupling. The automatic tuner circuit could predict the value needed to achieve resonance or a high Q factor based on the input frequency, or alternatively could employ a feedback system to self-tune as the input frequency changes. The automatic tuner circuit could further be employed to efficaciously control charging to decrease overall charging time. Differences in devices, patients and their environment will modify the Q factor of the system. An automatic turning circuit can automatically compensate for these changes.

In a still further embodiment, a feedback circuit or system could be further employed to automatically compensate for changes in the environment and patient load. The feedback circuit would tune charging based on input energy. Alternatively, the feedback circuit method is to know what is coming and instantly auto tune the charging circuitry based on the pattern that will be sent shortly to the IMD 10.

The feedback system could also be used to provide positive feedback to the patient. For instance, the modulation frequency could produce a very "futuristic" sound, such as a low to high frequency ramp, which repeats at a predetermined interval, or could even play a song, perhaps of the patient's choosing. Further, the modulation frequency could be used to signal to the user the state of the device, such as charging, error condition, or completion of charging.

Encasement

The power source may optionally be encased in a metallic cylindrical case that also functions as an electrical feedthrough, where the outside of the power source case is used as a conductor to the electrode connection. Conventional IMDs are typically rectangular or prismatic in shape. A cylindrical shape offer several advantages, including patient comfort, power source design, accommodations for different types of antennae, and improved insertability and ease of explant.

The actual electrode contact area forms a hollow dome to absorb any swelling that might occur during the extremely unlikely event of a catastrophic power source failure. A set of feedthroughs, arranged in a possible pattern of [+/Temp/−/chassis] is provided to provide increased safety, reduction of leakage currents and ease of assembly.

In one embodiment, the power source case is electro polished to improve the ability of the receiving coil 36 to slide over the power source case during installation. In a further embodiment, the head of the power source, that is, the end of the power source that faces outwards away from the flexible circuit board 30 and replaces the "Protectrode" assembly. The head is formed of thin titanium and shaped as a dome to serve as an electrode and provide internal relief for power source expansion if a failure occurs.

Chemistry

In one embodiment, the power source can use lithium titanate (LTO) technology. Alternatively, other power source or battery technologies such as Lithium Cobalt Oxide, Lithium Manganese Oxide, Lithium Nickel Manganese Cobalt Oxide, Lithium Iron Phosphate, Lithium Nickel Cobalt Aluminum Oxide, Nickel Cadmium or Nickel Meta Hydrate could be employed.

To accommodate complete discharge without oxidation of the power source collector, the copper collector typically found in a power source could be replaced by a corrosion resistant metal, such as stainless steel, titanium, gold or platinum. Furthermore, a collector could be made of a standard base metal and plated to increase corrosion resistance. This combination of materials could be copper, nickel, palladium, gold or titanium, gold, or stainless steel, gold or any appropriate combination thereof to provide the necessary degree of corrosion resistance and zero volt life. The surfaces of the materials and platings could be roughened to increase surface area and provide better charge and discharge characteristics.

Scalloped Electrodes

Figure 11:
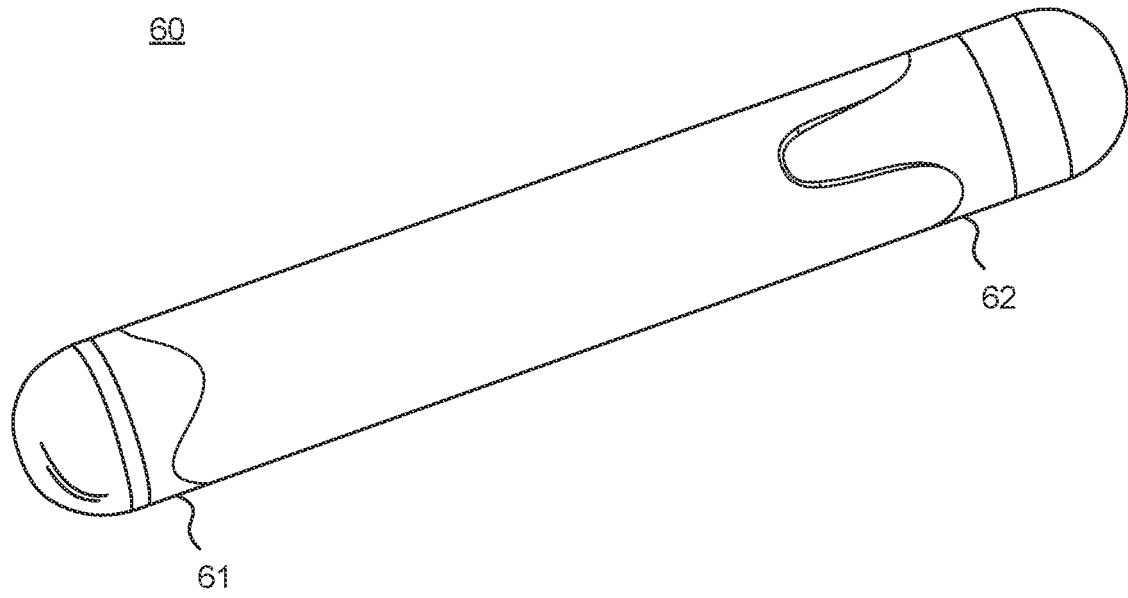
FIG. 11 is an outer perspective view showing an IMD that houses a configurable hardware platform for physiological monitoring of a living body in accordance with a further embodiment.

The proximity of the high frequency antenna 34 to the conductive surface 18 exposed on the outside surface of the tubular body 11 can, in some circumstances, pose a risk of ECG signal degradation. FIG. 11 is an outer perspective view showing an IMD 60 that houses a configurable hardware platform for physiological monitoring of a living body in accordance with a further embodiment. The electrode 61 formed as part of the "Protectrode" section of the IMD 60 and the electrode 62 formed on the outer surface of the tubular body 11 are shaped with scalloped cutouts on their respective inward facing aspects. The electrode formation minimizes potential parasitic coupling of the electrodes 61 and 62 to ground strips that are used for the high frequency antenna return. In addition, the shape of the "Protectrode" electrode 61 increases the performance and durability of the ceramic to titanium weld joints, when used, to join the "Protectrode" 12 to the tubular body 11.

Microarchitecture

Figure 12:
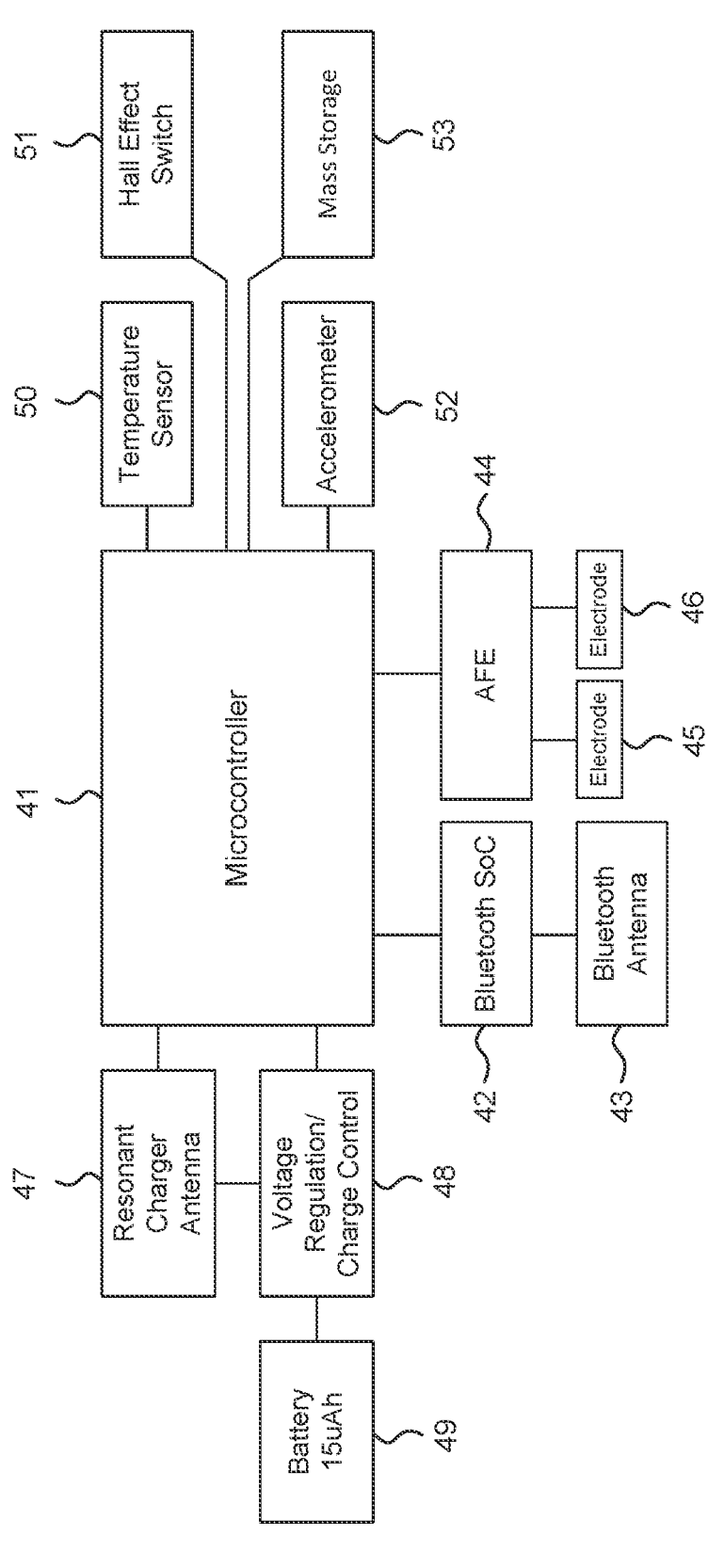
FIG. 12 is a block diagram showing the microarchitecture of the IMD of FIG. 1.

The operation of the IMD 10, including data capture, analysis, and communication, is controlled by a programmable microcontroller. FIG. 12 is a block diagram showing the microarchitecture 40 of the IMD 10. The microcontroller is remotely interfaceable over a wireless radio frequency (RF) data communications link using the high frequency antenna 34 that is housed within the "Protectrode" 12, which enables the IMD 10 to provide continuous heartbeat-by-heartbeat monitoring and to be remotely reconfigured or reprogrammed to utilize one or more of the physiological sensors.

Microcontroller

In one embodiment, a low power, high efficiency microcontroller 41, such as a microcontroller from the RL78 family of microcontrollers offered by Renesas Electronics Corp., Tokyo, Japan, can be used. Architecturally, the microcontroller is built around a Harvard architecture that physically separates signal and storage pathways for instructions and data storage. The microcontroller operates under a dedicated microprogram stored as microcode within a non-volatile memory device, rather than a general purpose operating system, which aids in efficient operation and longer power source life, although in a further embodiment, an operating system including a real time operating system, could be used. Note that there is memory located on the microcontroller as well as externally and program instructions are expected to be stored in the microcontroller's flash memory.

Additional Components

The microcontroller 41 is interfaced to components, both integrated and off-chip, that provide continuous and extensible monitoring capabilities to the IMD 10. A voltage regulation/charge control circuit 48 is interfaced to the low frequency resonant charger antenna 47 and the microcontroller 41, which together regulate and control the charging of the power source 49. An integrated Bluetooth system-on-a-chip (SoC) transceiver circuit 42 is similarly interfaced to the high frequency antenna 34 and the microcontroller 41 to provide data communications capabilities to the IMD 10. An electrode dipole is formed by electrodes 45 and 46, which are interfaced to an analog front end (AFE) 44 and to the microcontroller 41 to effect electrocardiographic monitoring. In one embodiment, temperature, actigraphy, and motion sensing are respectively provided through a temperature sensor 50, Hall effect switch 51, and accelerometer 52. Finally, monitoring data, including continuous ECG data awaiting offloading, are stored in mass storage 53 in the form of random access memory.

Paradigm

Purpose-build IMDs, such as implantable cardiac monitors (ICMs), are specifically designed to address a range of potential conditions which would be observable over an expected patient population. Thus, typical ICMs require power hungry and complex signal filters, which are able to detect R-wave intervals on a very high percentage of the patient population. Practically, however, the majority of the patient population does not need extreme filtering. As a result, dramatic power savings are possible if a signal filter could be selected that is appropriate for a given patient and for patients with special needs, strong signal filtering can be selected to reduce false positives at the cost of high power consumption and frequent recharging.

Here, the IMD 10 implements a configurable hardware platform based on a reprogrammable microcontroller that can be supplemented with additional physiological sensors, including an SpO$_2$ sensor, a blood pressure sensor, a temperature sensor, respiratory rate sensor, a glucose sensor, an air flow sensor, and a volumetric pressure sensor, and non-physiological sensors, including an accelerometer and inertial motion sensor. Through the microcontroller 41, the sensors can be selectively activated over the implantation lifetime, whether in real time or during reprogramming, to tailor the monitoring of the patient to ongoing diagnostic needs.

The microcontroller-based design also affords the flexibility to choose signal filtering and processing algorithm options tailored to each patient. This microarchitecture allows the best patient experience by eliminating designs that adopt a one-size-fits-all approach and which are dominated by considerations of accommodating the hardest cases. The microarchitecture further accommodates changes to patient morphology; modifications to the filtering software can be selected dynamically and updated in the field as a configuration update that is pushed by a physician from the "cloud," that is, the server paradigm that virtualizes server-side functionality as a service widely available through access to the internet or other wide-area data communications network.

In a further embodiment, the transceiver 42 can be used in conjunction with the microcontroller to communicate with ingestible sensors, such as offered by *Proteus* Digital Health, Inc., Redwood City, CA. Ingestible sensors are pills made of biocompatible materials, which combine remote monitoring microelectronics with medication or inert materials that can safely be taken by a patient. Typically, an ingestible sensor is activated by gastric fluids dissolving or acting upon its surface, after which the sensor begins to measure gastro-intestinal tract physiology and, possibly, other types of physiology. Ingestible sensors that are capable of communicating wirelessly, such as over Bluetooth, Medradio, or via WiFi, are available as a real-time-capable alternative to standalone ingestible sensors that store recorded physiology onboard the device. This wireless-capable class of ingestible sensors allows the sensory data to be captured in real time. Moreover, these types of ingestible sensors aAcan be coupled with the IMD 10; thus, a patient can be monitored for medication compliance by providing accurate, time-correlated data that can be used to evaluate non-adherence and to provide positive reinforcement. The patient's caregiver can be notified in real time as to a patient's behavior with respect to adhering to prescribed medication.

The platform described facilitates the monitoring of every heartbeat in contrast to conventional non-rechargeable platforms, which typically do not have enough power to store and transmit each heartbeat. In addition to monitoring each heartbeat, since the heartbeats are offloaded, the heartbeats may be analyzed by an intelligent algorithm not located in the platform proper, which allows for better recognition of arrhythmias and disease conditions, as the complexity of the algorithm is not limited by the amount of power available to the analyzing device.

Figure 13:
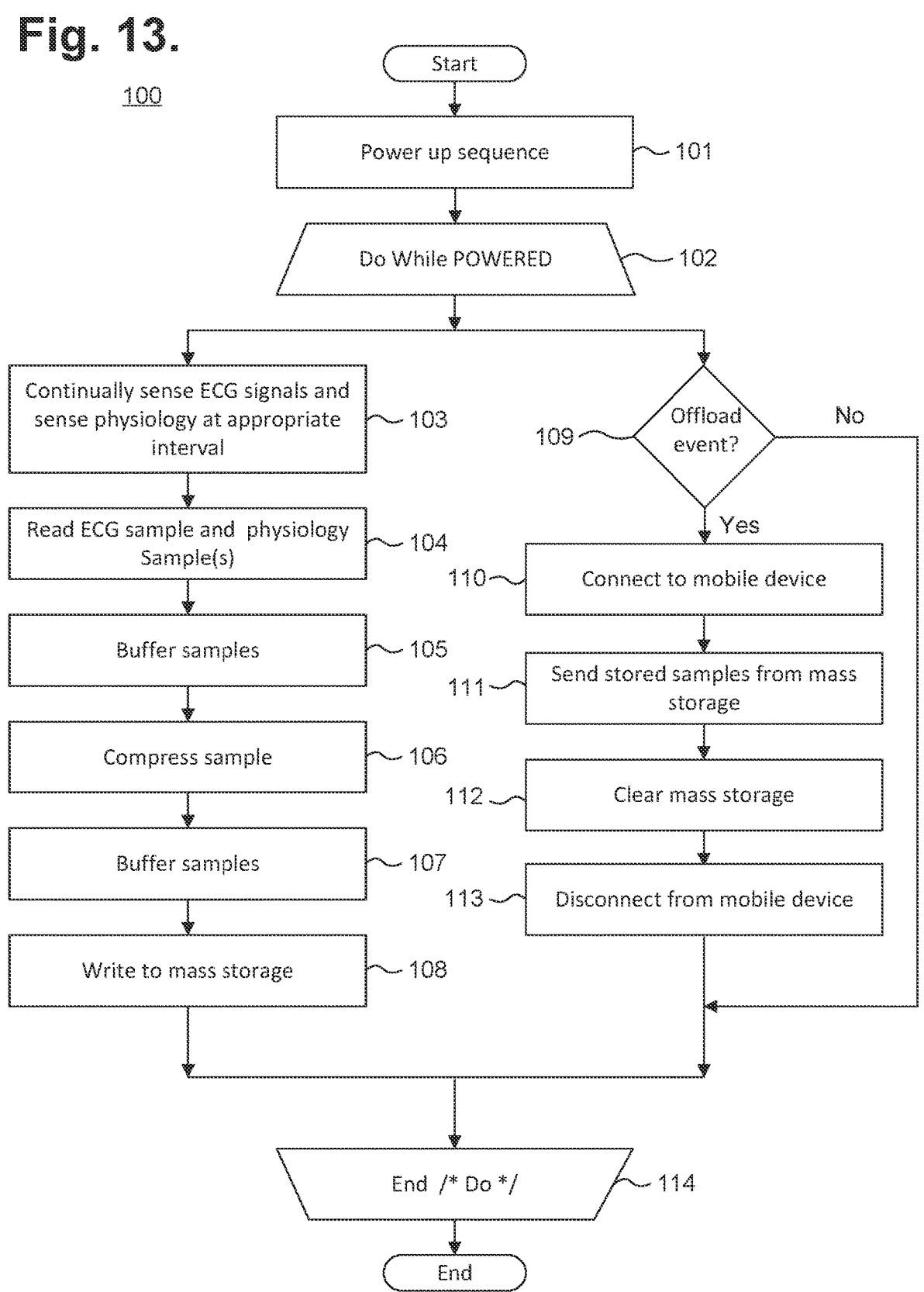
FIG. 13 is a flow diagram showing a method for continuously monitoring electrocardiography for use in the IMD of FIG. 1.

The IMD 10 continuously monitors the patient's heart rate on a heartbeat-by-heartbeat basis and physiology. FIG. 13 is a flow diagram showing a method 100 for continuously monitoring electrocardiography for use in the IMD 10 of FIG. 1. Initially, following successful implantation, the microcontroller 41 executes a power up sequence (step 101). During the power up sequence, the voltage of the power source 49 is checked, the state of the mass storage (flash memory) 53 is confirmed, both in terms of operability check and available capacity, and microcontroller operation is diagnostically confirmed.

Following satisfactory completion of the power up sequence, an iterative processing loop (steps 102-114) is continually executed by the microcontroller 41. During each iteration (step 102) of the processing loop, the AFE 44, through the electrode dipole created by electrodes 45 and 46, continually senses electrocardiographic signals; additionally, patient physiology is sampled at appropriate intervals, depending upon the sampling frequency selected for the particular type of physiology being sensed (step 103). One or more types of physiology can be sensed at any given time. The type and sampling rate of physiology are selectively activated over the lifetime of the IMD 10 via the microcontroller 41 through programmatic control, which in turn, determines the hardware device being utilized. For instance, reading patient temperature once each minute would require activation of the temperature sensor 50. A similar approach to sensing non-physiological data, such as position or posture, is followed mutatis mutandis.

A sample of the ECG signal and, at appropriate intervals, physiology, are read (step 104) by the microcontroller 41 by sampling the AFE 44 and appropriate physiology sensing hardware. Each sampled ECG signal and each of the physiology signals, in quantized and digitized form, are temporarily staged in a buffer (step 105), pending compression preparatory to storage in the mass storage 53 (step 106). Following compression, the compressed ECG digitized samples are again buffered (step 107), then written to the mass storage 53 (step 108) using the communications bus. Processing continues (step 114), so long as storage space remains available in the mass storage 53, after which the processing loop is exited. Still other operations and steps are possible.

The IMD 10 processes sensing signals generated by ingestible sensors follow a similar methodology as with processing monitored physiology, with two important distinctions. First, ingestible sensors are typically activated upon ingestion and thereafter generate monitoring data only during the time in which they are present in the patient's digestive tract. Second, ingestible sensor data is generally time-sensitive, where the correlation of the time of signal generation and time of day is of notable interest in itself, whereas physiological data is typically seen in the context of other physiological events, such as SpO$_2$, which is significant with reference to cardiac events.

Concurrently, the IMD 10 can offload stored monitoring data to a datacenter or other external device. The data is offloaded in a conceptually-separate execution thread as part of the iterative processing loop (steps 102-114) continually executed by the microcontroller 41. If an offloading event occurs (step 109), the IMD 10 connects to a mobile device (step 110), such as a smart phone or cellular-enabled tablet, and the stored samples are sent from the mass storage 53 to the mobile device (step 111). In turn, the mobile device relays the uploaded ECG and physiology samples to the datacenter. Alternatively, the IMD 10 can connect directly to the datacenter, provided the transceiver 42 is sufficiently capable. The mass storage 53 is cleared (step 112) and the IMD 10 disconnects from the mobile device (step 113) upon completion of the sending of the stored samples. Processing continues (step 114). Still other operations and steps are possible.

While the invention has been particularly shown and described as referenced to the embodiments thereof, those skilled in the art will understand that the foregoing and other changes in form and detail may be made therein without departing from the spirit and scope.

What is claimed is:

1. An implantable medical device (IMD), comprising:
   a housing comprising a hollow body forming a first sensing electrode on an outer surface and a first end cap and a second end cap affixed to opposite ends of the hollow body, wherein the first end cap comprises an electrically conductive semi sphere that serves as a second sensing electrode, the first sensing electrode comprising an electrically conductive surface that is an integral part of a portion of the outer surface of the hollow body and that is separated from the first end cap by an electrically insulated further portion of the outer surface of the hollow body; and
   an analog front end within the housing and electrically interfaced to the first and the second sensing electrodes and operable to sense electrocardiographic signals via the first and the second sensing electrodes;
   a transceiver circuit within the housing and operable to wirelessly communicate with an external device;
   a memory within the housing; and
   a microcontroller within the housing and operable under program instructions to continuously sample at least some of the electrocardiographic signals, to store the samples into the memory, and to offload the memory to the external device via the transceiver circuit.

2. The IMD in accordance with claim 1, wherein the second end cap comprises an electrically insulated semi sphere formed from a medical implantation-safe grade material comprising at least one of an acrylic, glass, ruby crystal, or ceramic.

3. The IMD in accordance with claim 1, further comprising a high frequency antenna interfaced to the transceiver circuit within the second end cap.

4. The IMD in accordance with claim 3, further comprising:
   a filler material within the second end cap and holding the high frequency antenna in place.

5. The IMD in accordance with claim 1, wherein the electrocardiographic signals are providing to the microcontroller as an analog signal.

6. The IMD in accordance with claim 1, further comprising a set of concave dimples formed along an inside shelf surface of the one end cap.

7. The IMD in accordance with claim 6, the first end cap further comprising:
   an insulator ring bonded to the electrically conductive semi sphere; and
   a metallic weld ring bonded to the insulator ring and to the hollow body.

8. The IMD in accordance with claim 7, the metallic weld ring comprising a chamfered edge bonded to the hollow body.

9. The IMD in accordance with claim 7, wherein the concave dimples facilitate bonding of the electrically semi sphere to the insulator ring.

10. The IMD in accordance with claim 7, wherein the first end cap is filled with a filler comprising one or more of an epoxy and silicon.

11. The IMD in accordance with claim 10, wherein the insulator ring comprises one or more of a ruby, glass, and ceramic and at least some of the filler is bonded to the insulator ring.

12. The IMD in accordance with claim 7, wherein the electrically conductive semi sphere, the insulator ring, and the metallic weld ring are bonded together using one of pressure fitting, brazing, laser welding, and electron beam welding.

13. The IMD in accordance with claim 1, further comprising:
   a cavity formed inside the first end cap;
   a circumferential groove longitudinally defined within the cavity, wherein a circuit board mounts within the groove.

14. The IMD in accordance with claim 13, further comprising:
   the circuit board comprising edges plated with a set of electrically conductive coatings.

15. The IMD in accordance with claim 14, wherein the electrically conductive coatings comprise a copper coating applied on the edges, a nickel coating applied on top of the copper coating, a palladium coating applied on top of nickel coating, and a gold coating applied on top of the palladium coating.

16. The IMD in accordance with claim 14, wherein the circuit board comprises copper traces and the electrically conductive semi sphere comprises titanium and the electrically conductive coatings inhibit a galvanic reaction between the copper traces and the titanium.

17. The IMD in accordance with claim 1, wherein the electrically insulated further portion of the outer surface is formed due a polymer-based coating applied to the further portion of the outer surface.

18. The IMD in accordance with claim 17, wherein the polymer-based coating is at least one of a Parylene C coating and a silicone polymer-based coating.

19. The IMD in accordance with claim 18, wherein the silicone polymer-based coating is applied over the Parylene C coating on the further portion of the outer surface.

\* \* \* \* \*